(12) United States Patent
Holzner et al.

(10) Patent No.: US 7,538,078 B2
(45) Date of Patent: May 26, 2009

(54) STABILIZED LIQUID RINSE-OFF COMPOSITIONS COMPRISING FRAGRANCED AMINOPLAST

(75) Inventors: Günter Wolfgang Holzner, Grand-Lancy (CH); Glenn Paul Johannes Verhovnik, Chene-Bougeries (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/669,745

(22) Filed: Jan. 31, 2007

(65) Prior Publication Data

US 2007/0123442 A1   May 31, 2007

Related U.S. Application Data

(63) Continuation of application No. PCT/IB2005/002386, filed on Aug. 9, 2005.

(30) Foreign Application Priority Data

Aug. 20, 2004   (EP) .................................. 04104019

(51) Int. Cl.
C11D 3/37 (2006.01)
(52) U.S. Cl. ........................ 510/441; 510/473; 510/475; 510/476
(58) Field of Classification Search ................ 510/441, 510/473, 475, 476
See application file for complete search history.

(56) References Cited

U.S. PATENT DOCUMENTS

| | | | |
|---|---|---|---|
| 4,234,627 A | 11/1980 | Schilling | 427/242 |
| 4,406,816 A | 9/1983 | Sliwka | 521/69 |
| 4,460,732 A | 7/1984 | Buscall et al. | 524/460 |
| 5,908,618 A | 6/1999 | Lorant | 424/70.5 |
| 6,284,281 B1 | 9/2001 | Chevalier et al. | 424/489 |
| 6,329,057 B1 * | 12/2001 | Dungworth et al. | 428/403 |
| 2003/0004226 A1 | 1/2003 | Hoffman et al. | 523/161 |
| 2003/0045447 A1 | 3/2003 | Heibel et al. | 510/329 |
| 2003/0171246 A1 | 9/2003 | Boeckh et al. | 510/475 |
| 2004/0071742 A1 * | 4/2004 | Popplewell et al. | 424/401 |
| 2004/0138093 A1 * | 7/2004 | Brain et al. | 512/4 |

FOREIGN PATENT DOCUMENTS

| | | |
|---|---|---|
| CH | 649 058 A5 | 4/1985 |
| DE | 198 33 347 A1 | 1/2000 |
| GB | 2 073 132 A | 10/1981 |
| WO | WO 98/28396 | 7/1998 |
| WO | WO 01/51197 A1 | 7/2001 |
| WO | WO 01/62376 A1 | 8/2001 |
| WO | WO 01/94001 A2 | 12/2001 |
| WO | WO 02/074430 A1 | 9/2002 |
| WO | WO 03/002699 A1 | 1/2003 |
| WO | WO 03/089561 A2 | 10/2003 |
| WO | WO 2005/017085 A1 | 2/2005 |

OTHER PUBLICATIONS

R. Wazinski et al., XP009042846,"Stabilisation of Beads In shower Gels", COSSMA, vol. 3 No. 4, pp. 420-443 (2002).
Ki-Jeong Hong et al. XP004362452"Preparation And Characterization Of Polyurea Microcapsules With Different Diamines", Material Research Bulletin, vol. 34, No. 6, pp. 963-969 (1999).
Kobayashi et al., "Solubilization properties of N-substituted amphiphilic acrylamide copolymers," Journal of Applied Polymer Science 73(12): 2447-2453 (1999).

* cited by examiner

*Primary Examiner*—John R Hardee
(74) *Attorney, Agent, or Firm*—Winston & Strawn LLP

(57) ABSTRACT

A liquid product comprising dispersed perfumed capsules and a thickening system which is a combination of non-ionic with cationic polymers. This allows a prolonged storage of the perfuming capsules without alteration of the latter and without the need to shake the composition before use in order to obtain an homogeneous composition of capsules. This further allows improved deposition of both the fragranced microcapsules and the cationic conditioning polymers onto target surfaces from rinse-off products.

15 Claims, No Drawings

STABILIZED LIQUID RINSE-OFF COMPOSITIONS COMPRISING FRAGRANCED AMINOPLAST

CROSS-REFERENCE TO RELATED APPLICATIONS

This application is a continuation of International application PCT/IB2005/002386 filed Aug. 9, 2005, the entire content of which is expressly incorporated herein by reference thereto.

TECHNICAL FIELD

The present invention relates to the perfume and consumer product industries. It concerns more particularly improved liquid and possibly sprayable compositions comprising aminoplast microcapsules containing fragrances, in particular fragranced melamine resin microcapsules intended to be used in consumer products traditionally fragranced. The invention is characterized by the fact that the compositions comprise specific combinations of polymers in the aqueous continuous phase of the consumer product, capable of keeping a homogeneous dispersion of the fragranced microcapsules and capable of depositing the microcapsules on target surfaces upon rinse application use. Further the specific combination of polymers reduces leakage of encapsulated fragrance from the microcapsules when they are dispersed into an aqueous rinse-off formulation.

BACKGROUND ART

Melamine resins and urea resins constitute the most important representatives of the amino resins. They result from a kind of Mannich type reaction between NH-containing compounds, nucleophilic molecules and carbonyl-containing compounds. NH-Components are mainly urea $H_2N$—CO—$NH_2$ or melamine (2,4,6-triamino-1,3,5-triazine). The carbonyl component is predominantly formaldehyde (rarely ketones or other aldehydes). Nucleophilic components may be H-acidic (halogen acids), OH compounds (alcohols, carboxylic acids), or NH compounds (urea, melamine, amines etc.) The resulting "aminoplastics" are colourless. Melamine resins are used for shatter-proof tableware. Moreover, the literature reports the use of amino resins for the encapsulation of active substances and mentions in particular the potential use of such encapsulation systems in perfumery and cosmetic applications. Therefore, amino resin based capsules, also commonly designated as aminoplast capsules, are the subject of a variety of literature reports and patent applications relating to the perfumery and cosmetic industries. In practice, these polymers are capable of forming a protecting shell around the active ingredient that one wishes to protect, thus providing an encapsulation system characterized by its water-insolubility. The active ingredient protected by the capsule may be released through mechanical rupture of the microcapsules, which become brittle when dry.

The process for the preparation of aminoplast microcapsules containing encapsulated fragrances is a well-known state of the art and is described in the patent literature, for Example in U.S. Pat. Nos. 3,516,941, 4,406,816, 4,976,961, DE Patent 198,33,347 (BASF), WO Patent 01/51197 (BASF) and U.S. Pat. No. 6,261,483 (BASF), GB Patent application 2073132 and WO 98/28396.

In the state of the art, preferred melamine/formaldehyde microcapsules are prepared in the presence of anionic emulsifying polymers that control particle size distribution and dispersion of the resulting capsules during their preparation. Furthermore, the preferred anionic melamine/formaldehyde microcapsules are known to be highly impermeable to the encapsulated ingredients.

The use of such fragranced aminoplast capsules in liquid formulations for household and cosmetic applications is also well-known. For example, U.S. Pat. No. 5,188,754, assigned to Procter & Gamble, describes detergent compositions which contain perfumes in the form of friable microcapsules. U.S. Pat. No. 5,137,646, also to Procter & Gamble, describes the preparation and use of perfumed aminoplast particles which are stable in fluid compositions such as fabric softeners. However, this composition requires a two-step manufacturing process where the perfume is firstly solidified with a meltable polymer, followed by grinding of the solidified perfume and coating with the aminoplast resin.

It is also known that cationic transfer agents drive the deposition of such aminopast capsules on fabric, skin and hair. This is of particular importance when such aminoplast capsules are used in liquid rinse-off formulations like laundry detergents, fabric conditioners, shampoos, rinse-off hair conditioners and body washes.

U.S. Pat. No. 4,234,627, assigned to Procter & Gamble, discloses a liquid fragrance coated with an aminoplast shell further coated by a water insoluble meltable cationic coating in order to improve the deposition of capsules from fabric conditioners. In U.S. Pat. No. 4,973,422 (P&G), from 1989, it was then further described that capsules with a cationic coating provide improved substantivity to the surface being treated, such as fabric treated with a fabric softener. The same idea was described in 1991 in U.S. Pat. No. 5,185,155, assigned to Unilever, where the selection of cationic polymers was enlarged to water soluble polymers and the type of encapsulation was distinct from those in the state of the art at the time. Patent application US 20040071742, assigned to IFF, discloses a similar technology where the fragranced aminoplast capsules are coated with cationic starch or cationic guar.

However, such cationic coating procedures result in agglomeration of the capsules from the aqueous slurry. It is known in the art that the higher the cationic charge of the polymer, the faster the capsules will agglomerate. On the other hand a high cationic charge of the deposition polymer is desired to optimally drive deposition of the capsules during rinse applications. There is still a need to find a polymer combination that allows both cationic coating of the capsules and their homogeneous dispersion in the final aqueous slurry.

International patent application WO 03/002699, assigned to Colgate-Palmolive, describes fabric softening compositions where a cationic cross-linked polymer improves deposition of friable aminoplast microcapsules. In order to avoid agglomeration of the anionic capsules with cationic polymers, such cationic transfer agents are added to high dilutions of the fragranced aminoplast capsules in the final consumer base. The interaction of the capsules with the cationic deposition polymer is therefore limited and restricted by low concentrations of the capsules in the aqueous base. There is a need to optimize the deposition activity of such cationic polymers onto the capsule wall by increasing their direct contact with the aminoplast capsules in order to form a maximum cationic coating.

The improved deposition of cationic microcapsules in rinse-off formulations is also generally disclosed in US Patent application 2003/0171246, assigned to BASF, in US 2004007142 to IFF and in International patent application WO 01/62376, assigned to Henkel.

As previously mentioned, when cationic polymers are added to aqueous dispersions of aminoplast capsules, these capsules tend to agglomerate. In practical applications, the cationic polymers are added at low concentration to high dilutions of such aminoplast capsules. This reduces the formation of agglomerates liable to separate from the final rinse-off formulation.

However, the cationic coating of the aminoplast capsules is not very efficient and cannot be well controlled in order to maximize deposition of the capsules. Applying cationic coatings on aminoplast capsules through addition of cationic polymers to an aqueous dilution of such capsules will not lead to a uniform coating of these capsules and is therefore not efficient in increasing the protection of the encapsulated fragrance in such capsules against extraction by surfactants that are present in the rinse-off formulation.

Improved dispersion of melamine formaldehyde capsules in liquid formulations by adding dispersing agents is addressed in WO 03/089561 from P&G. Shear-thinning anionic and non-ionic polymers and silicas and bentonites are cited to prevent microcapsules from falling out of the solution. However, the invention does not address rinse-off formulations and the need to avoid agglomeration of anionic aminoplast microcapsules with cationic depositioning polymers.

As previously mentioned, the major down-side of the use of aminoplast capsules in rinse-off applications is that the perfumed capsules are not stable in such liquid formulations. The perfume gets extracted out/off the capsules by surface active ingredients in the formulation. So far, none of the aminoplast capsules described heretofore remain stable for 2 months at 45° C. in rinse-off formulations, i.e. under storage conditions that are encountered in many practical circumstances.

Some attempts have been made to increase the stability of such fragranced aminoplast capsules by modifying the capsules' membrane. For example, International patent application WO 02/074430, to Quest International, which outlines the above-mentioned stability problems of aminoplast capsules in aqueous surfactant-containing products, suggests a solution based on the use in the capsule shell of a second polymer comprising a polymer or copolymer of one or more anhydrides. It particularly describes improved stability in hair shampoo of aminoplast capsules prepared in the presence of ethylene(maleic anhydride) copolymer. While this solution improves the resistance of the capsules to degradation, it does not improve the deposition of such capsules during rinse-off applications.

Moreover, the resulting stability after 1 month at 37° C. is not sufficient for these applications.

On the other hand, WO 01/94001, assigned to Syngenta Ltd., mentions the possibility of having a solid permeable shell of a polymer resin having surface modifying compounds capable of reacting with isocyanate incorporated therein. While being based on the use of melamine resins, the latter shells have been modified so as to become permeable and, as a consequence, are susceptible of loosing the perfuming ingredients there-encapsulated through a diffusion process during the storage of the capsules in common consumer rinse-off formulations.

Therefore, the solutions provided until now by the prior art are not satisfactory.

The Applicant has also previously addressed this issue in patent application WO 2005/017085, wherein there is proposed a solution to the above-mentioned problem via the use of a special packaging system comprising two compartments, the fragranced aminoplast or coacervate capsules being lodged in a compartment which is separate from that which contains the surface-active ingredients commonly present in such rinse-off formulations. Although such a solution has proved to be a major improvement over previously described systems, because the fragranced aminoplast capsules have a lower density than other liquids which are generally used in liquid household and cosmetic formulations, the capsules may still tend to separate from the formulation. The same problem of separation applies when fragranced aminoplast capsules are added directly to liquid formulations where the density of the liquid is different from that of the encapsulated perfume. Such liquids include water, silicone oils, organic and mineral oils, alcohols, glycols and glycerine. It was observed that the lower the viscosity of the formulation is, the faster the capsules are likely to separate. Furthermore, the two-compartment packaging does not address the need to drive deposition of aminoplast capsules during rinse application onto the target surfaces.

In order to obtain a homogeneous dispersion of the capsules in a liquid formulation, this formulation needs to be thickened until it becomes a gel or a cream. Such thickened formulations are less convenient to dose and can no longer be easily sprayed.

We have now surprisingly discovered that by using specially selected combinations of water soluble or dispersible cationic and non-ionic polymers, dispersions of fragranced aminoplast or coacervate capsules can be stabilized in liquid formulations without reducing the flowability, spreading or sprayability of the dispersion.

SUMMARY OF THE INVENTION

The invention relates to liquid and possibly sprayable aqueous dispersions of fragranced aminoplast capsules which are effective as a rinse-off formulation. The aminoplast capsules are homogeneously dispersed thanks to a combination of cationic and non-ionic polymers which are present in the continuous aqueous phase of the consumer product and which are post-added after the preparation of the aminoplast capsules.

The combination of cationic and non-ionic polymers increases deposition of aminoplast capsules on the target surface during application of rinse-off consumer products. Moreover, the special combination of cationic and non-ionic dispersion agents makes it possible to obtain stable preparations of concentrated capsule dispersions that do not agglomerate.

We have found to our surprise that the combination of water soluble cationic and non-ionic dispersion agents in the continuous aqueous phase of the aminoplast capsules slurry enhances the perfume retention of the capsules during storage, in particular at elevated temperatures. This may be due to deposition of the cationic polymers onto the outside of the aminoplast capsule membrane resulting in an additional cationic coating.

We found to our surprise, that when we coated fragranced aminoplast microcapsules with a combination of organic cationic polymers and cationic silicone polymers, this did not only improve dramatically the dispersion stability of such capsules, but it also improved significantly the gloss and conditioning effect of such capsules on hair when applied from a hair shampoo. The coated aminoplast capsules were much more effective in conditioning and gloss-enhancing, compared to the separate addition of the same amount of uncoated aminoplast capsules, cationic polymer and cationic silicone polymer to the hair shampoo.

The compositions of the invention make it possible to provide perfumed rinse-off consumer products which are stable during storage even at high temperatures and which do not require separation of the aminoplast capsules from the surface-active components of such perfumed consumer liquid formulations.

DETAILED DESCRIPTION OF THE PREFERRED EMBODIMENTS

By "aqueous" dispersion it is meant here a composition essentially water based, possibly containing up to 97 or 98% by weight of water, relative to the total weight of composition, and typically containing at least 50% by weight of water, but which may also contain other solvents compatible with the capsules such as for example ethanol.

In a first embodiment of the invention, the fragranced capsules consist of melamine resin microcapsules. These microcapsules are conventionally prepared by a poly-condensation process comprising emulsifying the ingredient to be encapsulated, namely a perfuming ingredient or composition, in an aqueous solution of a melamin/formaldehyde resin, and then hardening the thus formed microcapsules. Suitable capsules for the purpose of the invention are commercially available by manufacturers such as BASF (under the tradename of MICRONAL®). Typically, these capsules will encapsulate from 20 to 85% by weight of perfume, relative to their total weight. Preferably, fragranced melamine resin capsules will be used in the form of a liquid aqueous suspension or dispersion. However, the capsules may also be used in the form of a dried powder, obtained after a drying treatment of a liquid suspension, e.g. via a spray-drying treatment carried out in a generally known manner.

The concentration of capsules in the aqueous suspension or dispersion of the invention will be typically comprised between 0.5 and 50% by weight, more preferably from 0.5 to 5% by weight, relative to the total weight of aqueous suspension.

The nature of the fragrance contained in the capsules is immaterial in the context of the invention, provided that it is compatible with the materials forming the capsules. It will be typically chosen as a function of the perfuming effect that is desired to achieve with the dispersion or consumer product of the invention, and it will be formulated according to current practices in the art of perfumery. It may consist of a perfume ingredient or composition. These terms can define a variety of odorant materials of both natural and synthetic origin, currently used for the preparation of perfumed consumer products. They include single compounds or mixtures. Specific examples of such components may be found in the current literature, e.g. Perfume and Flavor Chemicals by S. Arctander 1969, Montclair, N.J. (USA). These substances are well known to the person skilled in the art of perfuming consumer products, i.e. of imparting an odor to a consumer product traditionally fragranced, or of modifying the odor of said consumer product.

Natural extracts can also be encapsulated into the system of the invention; these include e.g. citrus extracts such as lemon, orange, lime, grapefruit or mandarin oils, or essentials oils of plants, herbs and fruits, amongst other.

In addition to the fragranced capsules, the perfuming dispersion of the invention may comprise optional ingredients such as antibacterial agents, cosmetic emollients, vitamins, cooling agents, softeners, lubricants, gloss enhancing agents or any other current active ingredient used in cosmetic or household applications, as long as the latter do not alter the capsules.

The dispersing aids present in the continuous aqueous phase of the melamine resin capsules slurry consist of a thickening polymer system that is a combination of non-ionic and cationic polymers. It was found in particular that further addition of cationic silicone polymers to the continuous aqueous phase of the capsule dispersion reduced significantly the total viscosity of the dispersion without having a negative effect on the dispersion stability.

Non-ionic polymers are known to efficiently stabilize aqueous dispersions of aminoplast capsules at high viscosity. However, the resulting high viscosity formulations can be difficult to spread and not easily flowable and sprayable. In addition, even when the viscosity has reached the state of a gel or cream, many non-ionic polymeric thickeners can become inefficient at high temperature causing some separation of the capsules at 45° C. or higher temperatures. This is due to the fact that such non-ionic thickeners have a reversed temperature dependence and can turn into low viscosity at elevated temperature. The use of non-ionic polymers on their own is therefore not an optimal solution to the capsules' stability problem.

Typical examples of such non-ionic polymers thus used include guar gums, hydroxyalkyl cellulose derivatives (for example, TYLOSE® from Shin Etsu and Clariant, KLUCEL® HF from Aqualon and NATROSOL® from Hercules), carrageenan (namely from Kelco), cellulose, starch, maltodextrines, polymeric sugar derivatives, xanthan, PVP/VA copolymers (namely LUVISKOL® VA from BASF).

The complex formation between anionic aminoplast capsules and cationic polymers is highly desired to drive the deposition of the capsules from rinse-off formulations onto the surfaces on which the latter are applied. Therefore, such cationic polymers are also known to be added to liquid dispersions of fragranced aminoplast or coacervate capsules.

Commonly used such cationic polymers comprise gelatine, quaternized hydrolisates of proteins (for example GLUADIN® WQT from Cognis); polyquaternium polymers as cited in the CTFA Cosmetic Ingredient Dictionary, like cationic cellulose derivatives (MERQUATS® 100 and UCARE® JR 30 M from Amerchol), cationic guars (COSMEDIA® Guar from Cognis), quaternized guars (JAGUAR® C-162 from Rhodia) cationic polyacrylates (SALCARE® SC 60 and SALCARE® Super 7 from Ciba, or EUDRAGIT® RL 30D from Röhm), cationic acrylamides (RHEOVIS® CDE from Ciba), polyquaternized polymers (like LUVIQUAT® Care from BASF), polyethylene imine (LUPASOL® P from BASF), quaternized polysiloxanes and emulsion polymerized aminosilicones (Q2-7224 from Dow Corning, Dow Corning 929 Emulsion, ABIL® Quat 3270 from Degussa, FORMASIL® 410 and SM-2059 from General Electric, SLM -55067 from Wacker). These cationic polymers do not only help melamine capsules to deposit well on target surfaces through rinse-off products, but also improve the conditioning/softness of the treated surface.

However, when such cationic polymers are added to aqueous dispersions of aminoplast capsules, it is not uncommon to observe some agglomeration and separation of the capsules.

We have now found that combinations of non-ionic polymers and cationic polymers provide the best dispersion stability of the aminoplast capsules in liquid rinse-off formulations. The advantage of the invention is that the polymer combination does not cause agglomeration and separation of the capsules and does not have a negative impact on the deposition effect of the cationic polymer on the anionic aminoplast capsule.

The non-ionic polymer protects the aminoplast capsule from agglomerating with the cationic polymer and the latter keeps the aminoplast capsules well dispersed even in low-viscosity formulations.

With this combination of non-ionic and cationic polymers, the total viscosity of the liquid formulation can be kept very low, such that the formulation is easy to disperse or to spray and spreads well on surfaces such as skin, hair and fabric, or household surfaces. The invention thus improves on the embodiments which resort to the use of only one type of thickening polymer as previously known and this is apparent from the examples presented further on.

Typical concentrations of thickeners in the above embodiments of the invention vary from 0.1 to 5%. In the combinations of non-ionic and cationic polymers used, the relative proportions of the latter are comprised in a range of 5:1 to 1:5. Preferably, comparable weight amounts of non-ionic and cationic polymer shall be used.

The aqueous dispersions or slurries of aminoplast capsules of the invention can take the form of finished consumer products.

Many examples of consumer product bases to treat a variety of surfaces can be found in art textbooks and other literature, including the patent literature, relating to liquid consumer products commonly perfumed and which may in particular resort to the use of perfume capsules of the melamine type. Such examples of typical literature are namely cited in the introduction above, but it goes without saying that the consumer products according to the invention can assume any form or formulation desired, and they typically contain a surfactant system which rendered prior known dispersions of fragranced aminoplast capsules, namely melamine resin capsules, unstable as far as the release of the perfume contained therein, or their stability in the dispersion, was concerned.

Therefore, the consumer product of the invention is a ready-to-use perfumed consumer product with a treating or cleaning activity, typically a hair leave-on or rinse-off preparation, a shampoo, a shower gel a liquid detergent for laundry or household, a liquid textile softener or yet a deodorant for laundry.

Furthermore, the specific combination of cationic and non-ionic dispersion polymers allows preparation of highly concentrated aminoplast capsule dispersions with a capsule content up to 50% by weight, and more particularly between 30 and 50% by weight, in water. In the presence of the non-ionic dispersion aid, the cationic polymers can even be covalently reacted to the surface of the aminoplast capsules without causing agglomeration or separation of concentrated aqueous dispersions, in spite of capsule contents of up to 50% by weight in the dispersion. A particularly effective dispersion stabilization at low viscosities was obtained with combinations of organic non-ionic polymers, organic cationic polymers and cationic silicone polymers added to the continuous aqueous phase of the capsule dispersion.

Moreover, our results indicate that conditioning polymers in hair shampoos can be more effectively deposited onto hair when they are first adsorbed or covalently bonded onto these microcapsules. Thus the invention also relates to methods of depositing the microcapsules and/or these polymers on surfaces such as hair and skin by using the aqueous dispersions of aminoplast capsules according to the invention.

The same technology can be applied to other additives able to deposit onto a target surface from rinse-off products like rinse-off conditioners, laundry detergents, fabric softeners, soaps or body washes.

The invention allows more effective deposition of both the fragranced microcapsules and the conditioning polymers from rinse-off products at very low concentrations of these additives.

We have now discovered that these microcapsules strongly drive the deposition of organic and silicone polymers onto hair which allows the formulator to further reduce the concentration of such conditioning polymers in rinse-off products, such as hair shampoos. By coating aminoplast microcapsules with conditioning polymers, these polymers obtain a defined particle size that is not changed after addition to surfactant-containing formulations, like hair shampoos. When the same polymers are added separately to hair shampoo, relatively high concentrations of conditioning polymers need to be added to hair shampoos in order to obtain a noticeable deposition and conditioning effect on hair.

When the same conditioning polymers are first adsorbed onto microcapsules which are then added to hair shampoo, the microcapsules further drive the deposition of these conditioning polymers onto hair which allows significant reduction of such polymers in the formulation. This discovery differs from the prior art where a coating of aminoplast microcapsules is expected to form by separate addition of cationic polymers and aminoplast microcapsules to the shampoo as described in US patent application 2004/0071742 to IFF. At high concentrations of both, capsules and polymers, this coating might occur even in the final rinse-off formulation, but our invention allows a significant reduction of both, microcapsules and conditioning polymers in such rinse-off formulations, while still providing for good deposition of the microcapsules and conditioning polymers onto the final target surface.

EXAMPLES

Example 1

Cationic Concentrate of Fragranced Aminoplast Capsules

A) Anionic melamine/formaldehyde capsules containing encapsulated liquid fragrance SPOUTNIK from Firmenich were prepared following the procedure described in Example 2 of International patent application WO 01/51197, the entire content of which is expressly incorporated herein by reference. The resulting dispersion of 40% of anionic aminoplast capsules had an average particle size of 3-10 microns. The dispersion contained 32% of encapsulated fragrance and had a viscosity of 200 cPs. Upon ageing at ambient temperature for 1 month the fragranced microparticles moved to the surface forming a hard layer due to the absence of a non-ionic thickening agent.

The amount of fragranced microcapsules in the dispersion was determined by Microwave Moisture Analyzer Model MMA 30 from Sartorius.

The amount of encapsulated fragrance was calculated from the solids content measured by the Microwave Moisture Analyzer. From the total solids measured (40%), the amount of non-volatile solids, which was added to the reaction, was substracted (8%) resulting in the amount of encapsulated perfume (32%). Any non-encapsulated perfume would evaporate during the microwave drying process.

The amount of non-encapsulated fragrance was further analysed by mild extraction of the capsule dispersion with isooctane. To 5 g of capsule slurry, 50 ml of isooctane were added and stirred with a magnetic stirrer for 10 min. The dispersion was filtered and injected into a gas chromatograph coupled with a mass spectrometer. The surface area of the peaks in the gas chromatograph were compared to a standard solution of liquid fragrance in isooctane.

Viscosity of the microcapsule dispersion was determined by Brookfield Viscosimeter Model DV-II+Pro with spindle 3 at 10 rpm.

Particle size of the microcapsules was determined by particle size analyser model Mastersizer S from Malvern.

B) Anionic melamine/formaldehyde capsules containing encapsulated liquid fragrance SPOUTNIK from Firmenich were prepared following the procedure described in Example 1-A). To the final aqueous capsule dispersion, a cationic polymer was added (1.25% of UCARE® JR 30 M, Polyquaternium-10 from Amerchol) and was allowed to react for 1 hour at 85° C. with the capsules to form a cationic coating on the capsule membrane.

The resulting dispersion of 40% of cationic aminoplast capsules had an average particle size of 100 microns and became a hard gel within several days at room temperature. This gel was no longer dispersible in water.

C) Example 1-B was repeated, but after the addition and reaction of the cationic polymer UCARE(® JR 30 M at 85° C., the dispersion was cooled down to 60° C. and 0.4% by weight of TYLOSE® 200,000YP2 (Hydroxyethylcellulose from Clariant) were added to the aqueous dispersion. The resulting dispersion of 40% by weight of aminoplast capsules had a viscosity of 5000 cPs, remained fluid upon storage of 2 months at 45° C. and could be easily dispersed in water. Average particle size was measured to be 30 microns.

D) Example 1-C was repeated and, after the completion of the reaction, 4% of FORMASIL® 410—cationic amino-silicone emulsion from General Electric—were added at room temperature to the dispersion. The resulting dispersion had a viscosity of 1000 cPs, remained extremely fluid upon storage for 2 months at 45° C. and provided even better dispersibility in water compared to Example 1-C.

The composition of Example 1-A), in the absence of the cationic polymer, provided particles with an average size of 3-10 microns. Cationic composition of Example 1-C) resulted in an average particle size of 30 microns which shows that the addition of the cationic polymer causes agglomeration of the melamine/formaldehyde capsules, which could however be controlled and contained by the addition of the non-ionic thickening polymer TYLOSE®.

The further following examples describe optimized preparation of cationic fragranced melamine-formaldehyde microcapsules:

E) Melamine/formaldehyde capsules containing encapsulated liquid fragrance SPOUTNIK from Firmenich were prepared following the procedure described in Example 1-A). To 56 parts of the final aqueous capsule dispersion, 30 parts of a 3% solution of SALCARET® SC 60, a cationic conditioning polymer from Ciba, and 14 parts of water were added and were allowed to react for 1 hour at 85° C. with the capsules, while mixing with a dissolver disk stirrer at 1500 rpm, to form a cationic coating on the capsule membrane. The dispersion was then cooled down to ambient temperature. Solids content was 32%, the amount of encapsulated perfume was 18% and final viscosity was 500 cPs. After storage of 1 month at 45° C. the dispersion formed a hard rubber due to continuous crosslinking of the capsules with the cationic polymer. Physical properties were analyzed by the methods described in Example 1-A).

F) Melamine/formaldehyde capsules containing encapsulated liquid fragrance SPOUTNIK from Firmenich were prepared following the procedure described in Example 1-A). To 56 parts of the final aqueous capsule dispersion, 30 parts of a 3% solution of SALCARE® SC 60, a cationic conditioning polymer from Ciba, were added and were allowed to react for 1 hour at 85° C. with the capsules, while mixing with a dissolver disk stirrer at 1500 rpm, to form a cationic coating on the capsule membrane. The dispersion was then cooled down to 60° C. and 10 parts of a 2% solution of TYLOSE®. MB200,000Y2 from Clariant and 4 parts of water were added under agitation and were allowed to disperse for 10 minutes. The dispersion was then cooled down to ambient. Solids content was 32%, the amount of encapsulated perfume was 18% and final viscosity was 1000 cPs. After storage of 1 month at 45° C. the viscosity increased to 20,000 cPs but did not form the hard rubber as found in Example 1-E).

G) Melamine/formaldehyde capsules containing encapsulated liquid fragrance SPOUTNIK from Firmenich were prepared following the procedure described in Example 1-A). To 56 parts of the final aqueous capsule dispersion, 30 parts of a 3% solution of SALCARE® SC 60, a cationic conditioning polymer from Ciba, were added and were allowed to react for 1 hour at 85° C. with the capsules, while mixing with a dissolver disk stirrer at 1500 rpm, to form a cationic coating on the capsule membrane. The dispersion was then cooled down to 60° C. and 10 parts of a 2% solution of TYLOSE® MB200,000Y2 from Clariant were added under agitation and were allowed to disperse for 10 minutes. The dispersion was then cooled down to ambient and 4 parts of FORMASIL® 410, cationic aminosilicone emulsion from General Electric, were added. Solids content of the final dispersion was 32%, the amount of encapsulated perfume was 18% and final viscosity was 500 cPs. After storage of 1 month at 45° C. the viscosity only slightly increased to 1,000 cPs and the dispersion remained extremely fluid.

The following Table I summarizes the properties of the cationic melamine formaldehyde microcapsules slurries obtained as described above in sections E, F and G).

TABLE I

| | Analytical Parameters | | | | |
|---|---|---|---|---|---|
| Example | Capsules Weight % | Weight % encapsulated perfume | Viscosity, 1 day after preparation | Viscosity after 1 month storage at 45° C. | Stability of the slurry after 1 month storage at 45° C. |
| I-E: capsules with SALCARE ® SC 60 (cationic organic polymer) | 32% | 18% | 500 cPs | rubber | rubbery, agglomerated |

TABLE I-continued

| Example | Capsules Weight % | Weight % encapsulated perfume | Viscosity, 1 day after preparation | Viscosity after 1 month storage at 45° C. | Stability of the slurry after 1 month storage at 45° C. |
|---|---|---|---|---|---|
| I-F: capsules with SALCARE ® SC 60 (cationic organic polymer) TYLOSE ® (non-ionic organic polymer) | 32% | 18% | 1000 cPs | 20,000 cPs | homogeneous creamy |
| I-G: capsules with SALCARE ® SC 60 (cationic organic polymer) Tylose (non-ionic organic polymer) FORMASIL ® 410 (cationic silicone polymer) | 32% | 18% | 500 cPs | 1,000 cPs | homogeneous liquid |

The examples show the good stabilization of the capsule dispersion in the presence of combinations of cationic organic polymers with cationic silicone polymers and non-ionic organic polymers.

Example 2

Stability and Deposition of Melamine Capsules On Hair From Hair Shampoo

When 1% of the above cationic concentrate of aminoplast capsules described in Examples 1-C) and 1-D) were added to a commercial hair shampoo comprising as surfactants Sodium Laureth Sulfate, Cocamidopropyl Betaine and Cocamide DEA, the capsules remained well on hair that was washed with this shampoo. After rubbing on the dried hair, a strong fragrance burst was noticed.

After ageing the shampoo containing the above-mentioned capsules for 3 months at 45° C., there was still a fragrance burst noticed on hair treated with this shampoo. 1% Of anionic concentrate of aminoplast capsules of Example 1-A) were added to the same shampoo, and the shampoo was applied on hair without rinsing. After rubbing on the dried hair, a strong fragrance burst was noticed. When the hair was rinsed with water, no fragrance burst was noticed after rubbing on the dried hair, because the capsules were washed off with the rinse water.

After ageing the shampoo with aminoplast capsules from Example 1-A) for 3 months at 45° C., there was no fragrance burst noticed on the dry hair, treated with this shampoo without rinsing. The encapsulated fragrance had been completely extracted from the capsules by the surfactants of the shampoo.

Example 3

Preparation and Use of a Hair Shampoo

A model hair shampoo was prepared as follows: 30 parts of TEXAPON NSO IS (Sodium Laureth Sulfate from Cognis), 6 parts of TEGO BETAINE F50 (Cocamidopropyl Betaine from Degussa) and 3 parts of GENAPOL-3 (Laureth-3 from Clariant) were mixed. To the blend, 60.5 parts of water were added, followed by 0.5 parts of Liquapar Optima (biocide from ISP). The pH was adjusted to 5.5 with citric acid. The resulting hair shampoo was transparent and had a viscosity of 2000 cPs.

To this shampoo, 0.5% of cationic fragranced aminoplast microcapsules from Example 1-G) where added. In a second test, 0.3% of anionic fragranced aminoplast microcapsules from Example 1-A) where added together with equal amounts of the same cationic conditioning polymers used in the preparation of cationic microcapsules of Example 1-G).

5 g of Asian hair tresses, of 13 cm length, were rinsed with water, washed with 1 g of the above hair shampoo samples and rinsed again.

Deposition of perfumed microcapsules on the hair was determined olfactively. The dry hair tress was smelled before combing. Then, the hair tress was combed 10 times with a fine comb and reevaluated for odor strength.

When the capsules deposit on the hair, they break during the combing process and release fragrance. The fragrance strength is directly related to the amount of capsules deposited onto the hair. The olfactive evaluation was done by 10 panelists, on a blind test, and the olfactive perception of the fragrance was rated on a scale from 0 (no perfume smell) to 10 (extremely strong perfume smell). The following Table II summarizes the results of these evaluations.

TABLE II

Deposition of fragranced microcapsules on hair through a model shampoo

| | Example | | |
|---|---|---|---|
| | 3-A | 3-B | 3-C |
| Additives to model hair shampoo | none | 0.5% cationic capsules (Example 1-G) equals: 0.1% perfume 0.02% FORMASIL ® 410 | 0.02% FORMASIL ® 410 0.16% SALCARE ® SC 60 (3% sol.) 0.3% anionic capsules |

TABLE II-continued

Deposition of fragranced microcapsules on hair through a model shampoo

| | Example | | |
|---|---|---|---|
| | 3-A | 3-B | 3-C |
| | | 0.16% SALCARE ® SC 60 (3% sol.) | (Example 1-A) equals: 0.1% perfume |
| Fragrance strength on dry hair before combing | 0 | 0 | 0 |
| Fragrance strength on dry hair after 10 times combing | 0 | 8 | 0 |

The results show that fragranced microcapsules deposit more effectively onto hair from a hair shampoo when they are coated with cationic polymers before addition to the shampoo.

When the same amount of capsules and cationic polymers are added separately to the shampoo, no effective deposition of the fragranced microcapsules could be obtained.

Example 4

Conditioning and Gloss Performance of Melamine Capsules On Hair From Hair Shampoo To the model shampoo described in Example 3-A), fragranced aminoplast microcapsules and a variety of different additives were added.

5 g of Asian hair tresses, of 13 cm length, were decontaminated for 10 minutes with a solution of 365 parts water, 135 parts hydrogen peroxide (35% solution), 0.5 parts TEXAPON NSO and 7.2 parts ammonia. The hair tresses were then rinsed with water, washed with 1 g of hair shampoo and rinsed again.

Dry and wet combability of the hair was determined by slowly passing a comb, with a teeth distance of 1 mm, through the hair tress until a first resistance to combing was noticed. The hair length that could be combed without any resistance was determined as being the combing length related to the combability of the hair tress. For each different treatment, 5 hair tresses were used and the average combing values are reported.

Gloss of the hair tresses was determined with a Micro-Tri-gloss meter from Byk Gardner. A higher value measured by the gloss meter indicates a higher refraction of light and therefore a higher gloss of the hair tress. The gloss was measured 5 times on each hair tress at a light angle of 60° and the average gloss values are reported. For each different treatment, 5 hair tresses were used and the overall gloss average values are reported in the following Table III which summarizes the results of these tests.

TABLE III

Conditioning and gloss performance of model hair shampoo containing various additives

| | Example | | | | |
|---|---|---|---|---|---|
| | 4-A | 4-B | 4-C | 4-D | 4-E |
| Additives to model hair shampoo | none | 0.02% FORMASIL ® 410 | 0.02% FORMASIL ® 410 0.16% SALCARE ® SC 60 (3% sol.) | 0.3% capsules (Example 1-A) equals 0.1% perfume + 0.02% FORMASIL ® 410 + 0.16% SALCARE ® SC 60 (3% sol.) | 0.5% capsules (Example 1-G) equals: 0.1% perfume 0.02% FORMASIL ® 410 0.16% SALCARE ® SC 60 (3% sol.) |
| Gloss on dry hair before treatment | 0.4 | 0.4 | 0.4 | 0.4 | 0.4 |
| Dry combability before treatment | 7 cm | 7 cm | 7 cm | 7 cm | 7 cm |
| Wet combability before treatment | 4 cm | 4 cm | 4 cm | 4 cm | 4 cm |
| Wet combability after shampooing | 2 cm | 4 cm | 5 cm | 5 cm | 8 cm |
| Gloss on dry hair after shampooing | 0.4 | 0.5 | 0.5 | 0.5 | 0.7 |
| Dry combability after shampooing | 6 cm | 7 cm | 8 cm | 8 cm | 13 cm |

TABLE III-continued

Conditioning and gloss performance of model hair shampoo containing various additives

|  | Example | | | | |
|---|---|---|---|---|---|
|  | 4-A | 4-B | 4-C | 4-D | 4-E |
| Fragrance strength on dry hair before combing | 0 | 0 | 0 | 0 | 1 |
| Fragrance strength on dry hair after combing | 0 | 0 | 0 | 1 | 8 |
| Shampoo stability after 1 month storage at 37 | transparent | transparent | transparent | agglomerated capsules | homogeneously dispersed capsules |

The results show that not only the microcapsules but also the conditioning polymers deposit more efficiently onto hair from a hair shampoo, when the conditioning polymers are bonded to the microcapsules before addition to hair shampoo (Example 4-E). When the same amount of conditioning polymers is added separately to the shampoo (Example 4-D), the resulting conditioning effect is significantly lower, indicating a lower deposition of such conditioning polymers onto the hair.

Example 5

Conditioning Performance of Melamine Capsules On Skin From Shower Gel

To the model shampoo described in Example 3-A), there were added fragranced aminoplast microcapsules and a variety of different additives.

Preparation and Use of Shower Gel

A model shower gel was prepared as follows: 30 parts of Tego Betaine F50 (Cocamidopropyl Betaine from Degussa) and 3 parts of Genapol-3 (Laureth-3 from Clariant) were mixed. To the blend, 65.5 parts of water were added, followed by 0.5 parts of Liquapar Optima (biocide from ISP). The pH was adjusted to 5.5 with citric acid and viscosity was adjusted with 1 part of sodium chloride. The resulting hair shampoo was transparent and had a viscosity of 5000 cPs.

Conditioning Performance of Melamine Capsules On Skin from Shower Gel

To this shower gel, 1.0% of cationic fragranced aminoplast microcapsules from Example 1-G) where added. In a second test, 0.6% of anionic fragranced aminoplast microcapsules from Example 1-A) where added together with equal amounts of the same cationic conditioning polymers used in the preparation of cationic microcapsules of Example 1-G). 10 panelists were asked to rinse the backs of their hands with warm water and then to apply 0.5 g of the two model shower gels. The gel was rubbed for 1 minute to create foam and was then rinsed with warm water until no foam remained anymore on the hands.

After 1 hour drying, the panelists were asked to evaluate which back of their hands felt softer. 8 from 10 pannelists considered the hand softer that was washed with the shower gel containing cationically coated microcapsules from Example 1-G).

The results are summarized in table below.

TABLE

Conditioning performance of model shower gel containing various additives

|  | Example | |
|---|---|---|
|  | 5-A | 5-B |
| Additives to model shower gel | 0.6% capsules (Example 1-A) equals 0.2% perfume + 0.04% FORMASIL ® 410 + 0.32% SALCARE ® SC 60 (3% sol.) | 1.0% capsules (Example 1-G) equals: 0.2% perfume 0.04% FORMASIL ® 410 0.32% SALCARE ® SC 60 (3% sol.) |
| Amount of panelists considering treated back of hand softer | 2 | 8 |

Example 6

Liquid Rinse-off Laundry Deodorant

The following compositions were prepared in a generally known manner with the following ingredients in the proportions indicated:

| Ingredients | 6-A weight % | 6-B weight % | 6-C weight % |
| --- | --- | --- | --- |
| De-mineralised water | q.s. 100 | q.s. 100 | q.s. 100 |
| Acrylamidopropyltrimonium chloride/ Acrylamide copolymer - 2% aqueous dilution (SALCARE ® SC60 from Ciba) | 40.0 | 40.0 | 40.0 |
| Hydroxyethylcellulose - 1% aqueous dilution (TYLOSE ® 60,000 from Clariant) | | 10.0 | 10.0 |
| Preservative (KATHON ® CG from Rohm/Haas) | 0.1 | 0.1 | 0.1 |
| 40% Dispersion of anionic aminoplast capsules containing 32% of encapsulated perfume (Example 1-A) | 4.0 | 4.0 | 4.0 |
| FORMASIL ® 410 (35% emulsion polymerised aminosilicone from General Electric Specialty Materials) | | | 1.0 |
| liquid perfume | 0.7 | 0.7 | 0.7 |
| Viscosity by Brookfield | 1200 cPs | 1404 cPs | 576 cPs |
| Stability after 3 months at 45° C. | separation | stable | stable |

When 20 ml of composition 6-B or 6-C were added to the dispenser box of a washing machine loaded with 3.5 kg of laundry, the aminoplast capsules deposited well on the fabric during the rinse cycle. On the dry fabric a strong fragrance burst was noticed after rubbing the textile. Similar deposition of aminoplast capsules could be obtained when the formulation of Example 6-C was mixed 1:1 with a commercial fabric softener, comprising a surfactant of the cationic esterquat type, and was then dosed by the dispenser of the washing machine.

Example 7

Liquid Rinse-off Hair Conditioner

The following compositions were prepared in a generally known manner with the following ingredients in the proportions indicated:

| Ingredients | 7-A weight % | 7-B weight % | 7-C weight % |
| --- | --- | --- | --- |
| De-mineralized water | q.s. 100 | q.s. 100 | q.s. 100 |
| Acrylamidopropyltrimonium chloride/Acrylamide copolymer - 1% aqueous dilution (SALCARE ® SC60 from Ciba) | 40.0 | 40.0 | 40.0 |
| Hydroxyethylcellulose - 2% aqueous dilution (KLUCEL ® HF from Aqualon) | | 20.0 | 20.0 |
| Preservative (LIQUAPAR ® Optima from ISP) | 0.1 | 0.1 | 0.1 |
| FORMASIL ® 410 (35% emulsion polymerised aminosilicone from General Electric Specialty Materials) | | | 1.0 |
| 40% Dispersion of anionic aminoplast capsules containing 30% of encapsulated perfume (Example 1-A) | 1.0 | 1.0 | 1.0 |
| Liquid perfume | 0.15 | 0.15 | 0.15 |
| Viscosity by Brookfield | 422 cPs | 707 cPs | 352 cPs |
| Stability after 3 months at 45° C. | separation | stable | stable |

When the formulations 7-B and 7-C were applied on wet hair and rinsed-off, good deposition of the fragranced aminoplast capsules could be obtained. After rubbing on the dried hair, a strong fragrance burst was noticed.

Similar deposition of aminoplast capsules could be obtained when these formulations 7-B and 7-C were mixed 1:1 with a commercial hair shampoo comprising as surfactants Sodium Laureth Sulfate, Cocamidopropyl Betaine and Cocamide DEA and was then applied on hair.

What is claimed is:

1. An aqueous slurry comprising fragranced aminoplast microcapsules and a thickening polymer system formed of a combination a cationic polyacrylate polymer, a hydroxyethyl cellulose and an emulsion polymerized amino silicone, wherein the thickening polymer system is present in an amount sufficient to act in combination as a stabilizing dispersion agent for the fragranced microcapsules and wherein the emulsion polymerized amino silicone is present in an amount sufficient to reduce the viscosity of the slurry.

2. The aqueous slurry according to claim 1, which contains from 0.5 to 50% by weight of the fragranced capsules, relative to the weight of the slurry.

3. The aqueous slurry according to claim 1, having a viscosity of between 1 and 10,000 mPa.

4. The aqueous slurry according to claim 1, having a viscosity of between 10 and 2,000 mPa.

5. The aqueous slurry according to claim 1, having a viscosity of between 10 and 200 mPa.

6. The aqueous slurry according to claim 1, wherein the aminoplast capsules are obtained from anionic melamine/formaldehyde resin capsules.

7. The aqueous slurry according to claim 1, wherein the stabilising polymers are hydrophilic and water soluble or water dispersable.

8. The aqueous slurry according to claim 1, wherein the silicone compound is present in an amount of 0.1 to 10% by weight, relative to the weight of the slurry.

9. The aqueous slurry according to claim 1, wherein the polymer combination is present in a weight range of from 0.1 to 5% by weight, relative to the weight of the slurry.

10. The aqueous slurry according to claim 1, wherein the thickening polymer system is present in a concentration of 0.1 to 5% by weight and the relative proportions of non-ionic and cationic polymer are comprised in a range of 5:1 to 1:5.

11. A consumer product, in the form of a cosmetic or household rinse-off or leave-on consumer product, comprising a slurry according to claim 1.

12. A consumer product according to claim 11, selected from the group consisting of a liquid detergent, a fabric softener, a hair shampoo, a hair conditioner, a liquid soap, a shower gel, a liquid all-purpose cleaner, a sprayable fabric freshener or a hair spray freshener.

13. A method to improve the deposition of aminoplast capsules or of a combination of a cationic polyacrylate polymer, an hydroxyethyl cellulose and an emulsion polymerized amino silicone on a surface, which comprises applying to that surface a consumer product according to claim 11.

14. A method for increasing the deposition of aminoplast capsules on a target surface during application of rinse-off consumer products according to claim 11, which comprises adding to the capsules or product a thickening polymer system formed of a combination of a polyacrylate polymer and an hydroxyethyl cellulose and an emulsion polymerized amino silicone, wherein the thickening polymer system is added in an amount sufficient to obtain stable preparations of concentrated capsule dispersions that do not agglomerate, so that perfume retention of the capsules is enhanced during storage of the product at room or elevated temperatures, and wherein the emulsion polymerized amino silicone is added in an amount sufficient to reduce the viscosity of the preparations.

15. A method to improve the deposition of aminoplast capsules or of a combination of a cationic polyacrylate polymer, an hydroxyethyl cellulose and an emulsion polymerized amino silicone on a surface, which comprises applying to that surface a slurry to claim 1.

\* \* \* \* \*

UNITED STATES PATENT AND TRADEMARK OFFICE
CERTIFICATE OF CORRECTION

PATENT NO. : 7,538,078 B2 Page 1 of 1
APPLICATION NO. : 11/669745
DATED : May 26, 2009
INVENTOR(S) : Holzner et al.

It is certified that error appears in the above-identified patent and that said Letters Patent is hereby corrected as shown below:

Title Page:
Item (54), after "AMINOPLAST" insert -- CAPSULES --. The title will then correctly appear as "STABILIZED LIQUID RINSE-OFF COMPOSITIONS COMPRISING FRAGRANCED AMINOPLAST CAPSULES".

Column 1:
Line 3, after "AMINOPLAST" insert -- CAPSULES --. The title will then correctly appear as "STABILIZED LIQUID RINSE-OFF COMPOSITIONS COMPRISING FRAGRANCED AMINOPLAST CAPSULES".

Column 20:
Line 12 (claim 15, line 5), before "to claim 1" insert -- according --.

Signed and Sealed this

Fourteenth Day of July, 2009

JOHN DOLL
*Acting Director of the United States Patent and Trademark Office*